United States Patent
Ihle et al.

(10) Patent No.: US 9,463,530 B2
(45) Date of Patent: Oct. 11, 2016

(54) METHOD FOR PRODUCING ANALYTICAL AIDS

(71) Applicant: Roche Diabetes Care, Inc.

(72) Inventors: Guenther Ihle, Mauer (DE); Hans List, Hesseneck-Kailbach (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/274,000

(22) Filed: May 9, 2014

(65) Prior Publication Data

US 2014/0243866 A1 Aug. 28, 2014

Related U.S. Application Data

(63) Continuation of application No. PCT/EP2012/072113, filed on Nov. 8, 2012.

(30) Foreign Application Priority Data

Nov. 10, 2011 (EP) .................................. 11188643

(51) Int. Cl.
*B23K 26/36* (2014.01)
*A61B 5/15* (2006.01)
*A61B 5/151* (2006.01)

(52) U.S. Cl.
CPC ........... *B23K 26/362* (2013.01); *A61B 5/1411* (2013.01); *A61B 5/151* (2013.01); *A61B 5/150022* (2013.01); *A61B 5/150282* (2013.01); *A61B 5/150419* (2013.01); *A61B 5/150435* (2013.01); *B23K 26/361* (2015.10); *A61B 5/15146* (2013.01); *A61B 5/15161* (2013.01)

(58) Field of Classification Search
CPC ...... B23K 26/00; B23K 26/14; B23K 26/16; A61B 5/1411; A61B 5/150022; A61B 5/150282; A61B 5/150419; A61B 5/150435; A61B 5/151; A61B 5/15146; A61B 5/15161
USPC ............ 219/121.65, 121.66, 121.83, 121.85, 219/121.67
See application file for complete search history.

(56) References Cited

U.S. PATENT DOCUMENTS

| | | | |
|---|---|---|---|
| 4,100,393 A | | 7/1978 | Luther |
| 4,777,096 A * | | 10/1988 | Borysko ........................ 428/571 |
| 5,225,650 A * | | 7/1993 | Babel et al. ............. 219/121.69 |
| 5,515,871 A * | | 5/1996 | Bittner et al. ................. 128/898 |
| 5,889,255 A | | 3/1999 | Bogart et al. |
| 2006/0228650 A1* | | 10/2006 | Matsuo .................. B23K 26/38 430/311 |
| 2008/0021346 A1* | | 1/2008 | Haar et al. .................... 600/583 |

FOREIGN PATENT DOCUMENTS

| | | |
|---|---|---|
| DE | 10034806 C1 | 12/2001 |
| DE | 10225451 A1 | 9/2003 |
| DE | 102007056112 A1 | 5/2009 |
| EP | 0038297 A1 | 10/1981 |
| WO | 2006066744 A1 | 6/2006 |

* cited by examiner

*Primary Examiner* — Brian Jennison
(74) *Attorney, Agent, or Firm* — Woodard Emhardt Moriarty McNett and Henry LLP

(57) ABSTRACT

A method for producing analytical aids for obtaining bodily fluid, in particular lancets or microsamplers, in which the aids are formed as a shaped part (10) from a flat metallic material by material separation on shaped part edges (28), wherein at least one sharp shaped part edge (28) is finished by laser irradiation, a laser beam (36) is guided repeatedly over the shaped part (10) along an irradiation path (38) in irradiation intervals, and the shaped part edge (28) is rounded by the cumulative energy input of the laser beam (36).

22 Claims, 2 Drawing Sheets

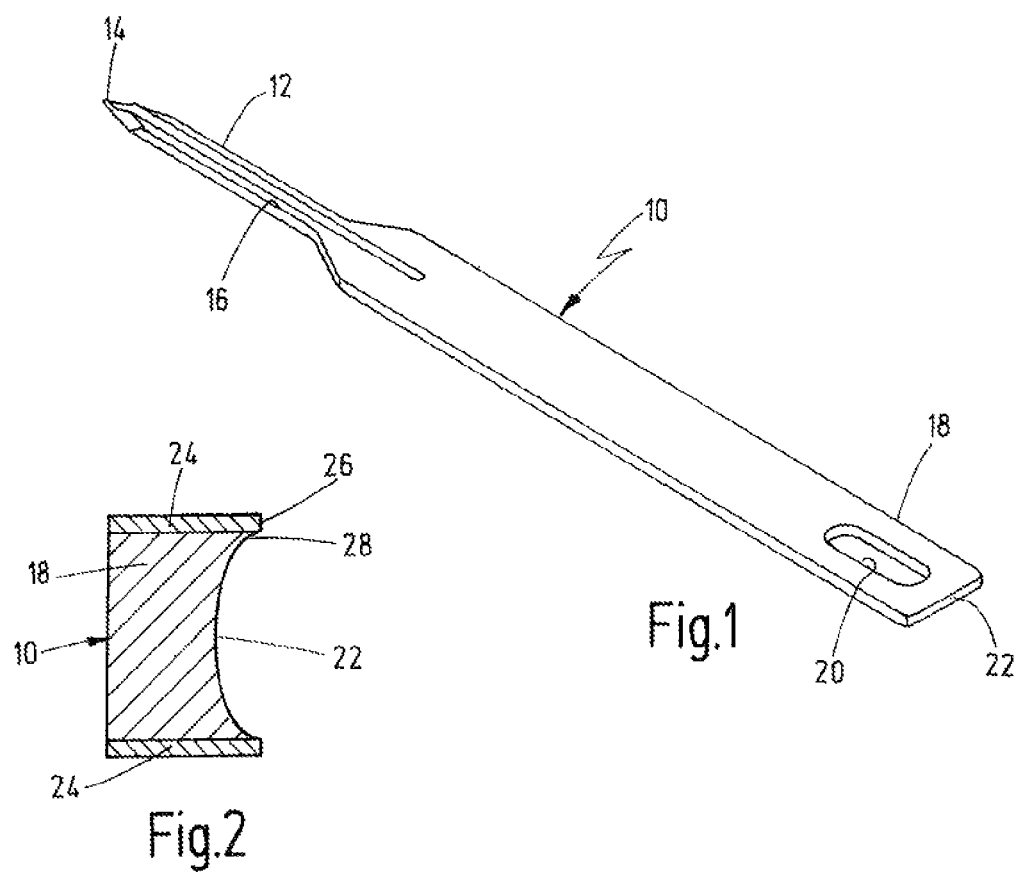
Fig.1
Fig.2
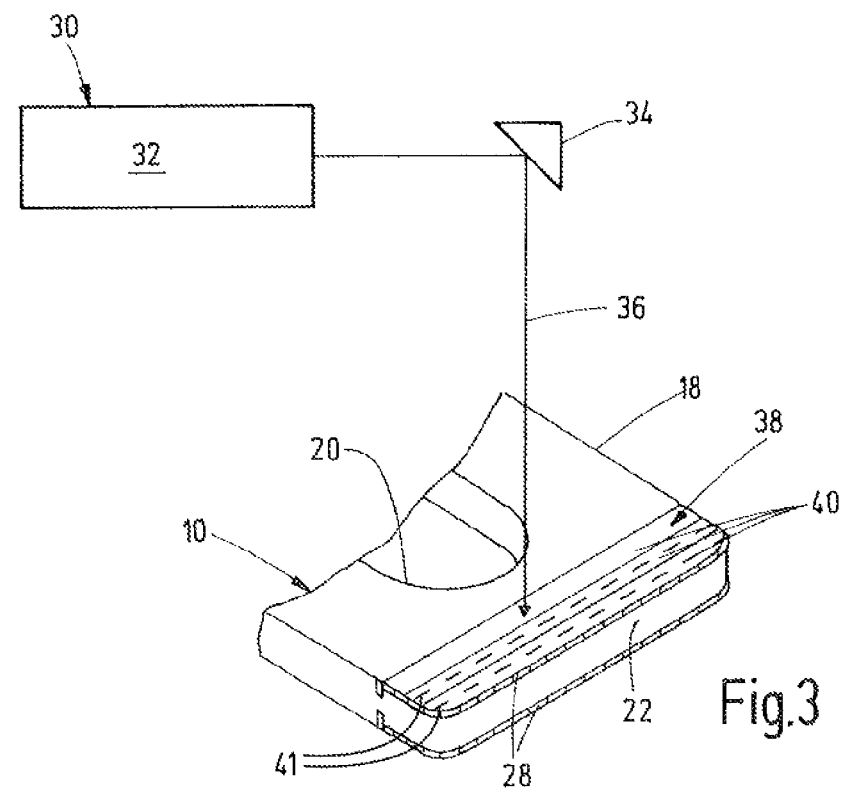
Fig.3

METHOD FOR PRODUCING ANALYTICAL AIDS

CROSS-REFERENCES TO RELATED APPLICATION(S)

This application is a continuation of and claims priority to International Patent Application No. PCT/EP2012/072113 which was filed on Nov. 8, 2012 which in turn claims priority to European patent application No. 11 188 643.8 filed on Nov. 10, 2011.

DESCRIPTION

The invention relates to a method for producing analytical aids for obtaining bodily fluid, in particular lancets or microsamplers, in which the aids are formed as a shaped part from a flat metallic material by material separation on shaped part edges. The invention also relates to an analytical aid for obtaining bodily fluid, produced by such a method.

In the field of diagnosis, in many cases it is necessary to obtain samples of bodily fluid, in particular blood samples or samples of interstitial fluid, in order to be able to detect the constituents thereof, in particular certain analytes. Examples of such analytes are blood glucose, clotting parameters, triglycerides, lactate or the like. Then, for example, an appropriate treatment may be decided upon according to the concentrations detected. In this case, one or more analytical aids are generally used as a disposable part by a subject himself, in order to obtain and/or analyze the samples of bodily fluid. Thus, for example, the analytical aids may comprise lancets which can be driven in order to execute a puncture movement so as to produce an opening in the subject's skin, through which the bodily fluid can be taken. Besides this, integrated test elements are also known which are used for collecting the bodily fluid sample as well as for sample transport, and optionally even for qualitative and/or quantitative analysis of this sample. Examples of such analytical aids are so-called microsamplers, in which a puncture or incision is produced by means of a lancet, and the sample is taken and transported to one or more test zones. These test zones may be arranged separately from the lancet, although they may also be a component of the lancet itself.

One technical challenge in the provision of analytical systems and analytical aids, however, is to provide them as economical mass-produced articles under suitable conditions with consistently high quality. In this context, for example, it has already been proposed in WO 2006/066744 A1 to form at least the base body of the disposable aid by mask etching as a shaped etched part from a flat metallic material. The etching process, however, makes the part edges extremely sharp. This is desirable at the lancet tip, but sharp edges in the holding region can be an impediment when carrying out the puncture process. In this case, during the puncture movement taking place to and fro, problematic contours may occur inside a guide or magazine chamber and/or material abrasion of problematic particles, which vitiate the analysis or block the collecting structures.

On the basis of this, it is an object of the invention to further improve the production methods known from the prior art, and correspondingly produced analytical aids, and in particular to ensure straightforward operation with low manufacturing outlay.

In order to achieve this object, the feature combination specified in the independent patent claims is proposed. Advantageous configurations and refinements of the invention may be found in the dependent claims. A method for producing an analytical aid is proposed, and an analytical aid is proposed, in which case the analytical aid may be producible by using a production method according to the invention. Accordingly, reference may be made to the description of the method in respect of possible configurations of the analytical aid, and vice versa.

The invention is based on the idea of achieving uniform edge rounding of problematic shaped part edges by multi-track laser irradiation. Thus, according to the invention it is proposed that at least one sharp shaped part edge is finished by laser irradiation, a laser beam being guided repeatedly along over the shaped part along an irradiation path in irradiation intervals, and the shaped part edge being rounded by the cumulative energy input of the laser beam. It is therefore possible to process structural regions in a controlled way even with microscopic dimensions and a compressed arrangement, without having to modify the workpieces or components in their macroscopic shape. The energy input in the individual irradiation intervals may be adjusted to be correspondingly low, in which case heat can be applied so to speak gently from the component side onto the edge to be processed, so that only the bladed edge sharpness is removed.

Surprisingly, it has been found that the edge rounding is optimized when the laser beam is guided into a region near the edge starting from a material region of the shaped part distant from the edge. Preferably, the laser beam is guided on tracks laterally overlapping one another starting from within the shaped part surface.

Further improvements can be achieved when the laser beam is guided on tracks laterally overlapping one another, and when the laser beam is guided in intervals with decreasing lateral offset from the shaped part edge.

In general, the laser beam should be guided at a lateral distance along the shaped part edge and preferably parallel thereto, in which case the lateral distance of the optionally also arced laser track from the shaped part edge may be slightly varied.

For production technology simplification, particularly with a view to magazining, it is advantageous that the shaped part edges to be processed, of a multiplicity of shaped parts, are arranged circularly, and that the laser beam is guided on a spiral path or in concentric circles over the shaped parts to the shaped part edges to be deburred. As an alternative, it is possible that the shaped part edges to be deburred, of a multiplicity of shaped parts, are arranged linearly, and that the shaped parts lying next to one another are scanned in lines with the laser beam.

For microscopic shaped part configuration, particularly in mass production, it is advantageous that a multiplicity of shaped parts are formed in an integrated etching process from a flat material piece in a star-shaped or linear arrangement, optionally connected by material bridges.

Advantageously, the aids are formed as a shaped part by mask etching. In this case, for particular shaped regions, for example lancet tips, it is advantageous that an optionally burred sharp shaped part edge is formed during the mask etching of the shaped parts by etching under a shaped part mask. Accordingly, the shaped parts can be formed with a sharp tip for insertion into the skin and optionally a collecting channel for bodily fluid in the region of the tip.

In order to avoid problematic contours, it is particularly advantageous that a shaped part edge is rounded in a coupling portion of the shaped parts formed for drive coupling.

In order to avoid structural damage, it is advantageous that the energy input of the laser beam in the individual irradiation intervals is set below the threshold for material ablation.

Advantageously, the number of irradiation intervals is predetermined in accordance with a desired edge dimension of a shaped part edge. It is particularly advantageous for the shaped part edge to be rounded with an edge radius of more than 30 μm, preferably about 50 μm.

The invention also relates to an analytical aid for obtaining bodily fluid, comprising a shaped part formed from a flat metallic material by mask etching, wherein at least one shaped part edge is rounded by laser irradiation on a multitrack irradiation path.

BRIEF DESCRIPTION OF THE SEVERAL VIEWS OF THE DRAWINGS

The invention will be explained in more detail below with the aid of the exemplary embodiments schematically represented in the drawing, in which:

FIG. 1 shows an analytical consumable formed as a microsampler, in a perspective representation;

FIG. 2 shows a proximal end section of the microsampler shaped by mask etching, in longitudinal section;

FIG. 3 shows a device for laser finishing of the microsampler in a diagrammatic representation; distal rear mask section in a representation corresponding to FIG. 1;

DETAILED DESCRIPTION OF THE INVENTION

Figure 4:
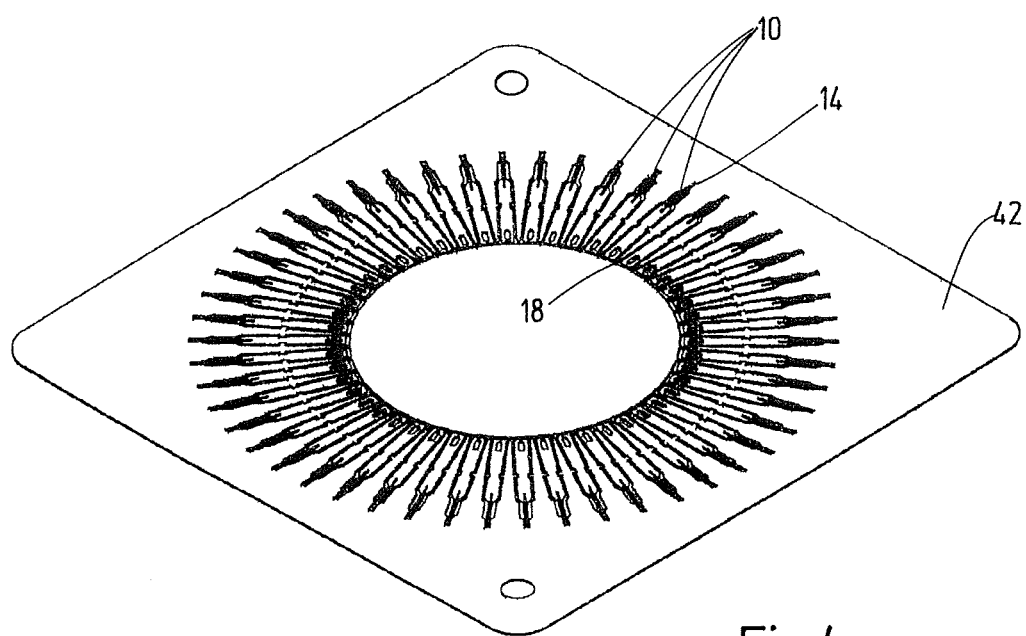
FIG. 4 shows another exemplary embodiment of a microsampler etched from a plate-metal piece, in perspective view.

The puncture and collection element 10 represented in FIG. 1 makes it possible, as a so-called microsampler, to collect bodily fluid (blood, tissue fluid) directly through a microscopic skin puncture for the detection of an analyte, for example glucose, in a hand-held device (not shown). To this end, the microsampler 10 comprises a puncture shaft 12 having a distal tip 14 and a groove-shaped collecting channel 16 for bodily fluid, as well as a proximal holding part 18 having a coupling portion 20 for drive coupling of a puncture drive of the hand-held device for executing a puncture movement. In order to avoid problematic contours in this case, laser finishing of the microsampler 10 formed by mask etching is provided in the region of a proximal rear edge 22, as will be explained below.

Such a microsampler 10 may be combined as an integrated diagnostic consumable having a test element for single determination of the analyte. In principle, the method according to the invention also relates to the production of lancets which are only configured in order to induce a puncture wound in a subject's skin.

As illustrated in FIG. 2, microsamplers 10 may be produced as etched shaped parts by mask etching from a metallic substrate, or flat material. In this case, an etching mask 24 is applied as a double-sided layout onto the two sides of a thin stainless steel substrate. The etching mask 24 may be structured by photolithography, that is to say from a photoresist by illumination and washing in a manner known per se, on the substrate. Through the holes in the etching mask 24 produced in this way, an etchant is subsequently applied to the substrate, the covered or masked regions being etched free in the basic shape and the etching mask 24 subsequently being removed. In this case, it should be taken into account that the material ablation does not only take place depthwise, but that undercut etching of edge contours 26 of the etching mask 24 also occurs. Further details are described for example in WO 2006/066744 A1, to which reference is made in this context.

As a result of undercut etching, extremely sharp shaped part edges 28 or burrs may be formed, which are desirable at the tip 14 but may be an impediment on the rear edge 22 when carrying out the puncture movement. In particular, during the puncture process, in which the microsampler 10 is moved within a guide, for example of a magazine consisting of relatively soft plastic, undesired edge engagement and material abrasion may occur.

In order to avoid such problems, laser finishing is provided in order to round, or deburr, the proximal shaped part edges 28. FIG. 3 illustrates a laser processing device 30 and the course of the laser beam guiding on the holding part 18 of the microsampler 10. By means of a laser 32 and a beam guiding instrument 34 known per se, a laser beam 36 is guided over the holding part 18 on a multitrack irradiation path 38 in a plurality of successive irradiation intervals, so that the proximal shaped part edges are rounded by the cumulative laser energy input. A laser system having a low beam power (about 10 W) may expediently be used for this, for example one which is available as a marking laser under the designation TruMark from the company TRUMPF Lasertechnik.

Starting from a material region of the holding part 18 separated from the edge 22, the laser beam 36 is guided on tracks 40 laterally overlapping one another as far as a region near to the edge, as indicated by dashed lines 41 in FIG. 3. The holding part 18 is therefore scanned with the laser beam 36 in intervals with a decreasing lateral offset parallel to the shaped part edges 28; the irradiation may take place simultaneously or successively on the two sides. The region of thermal influence on the material structure is in this case moved in intervals into the edge region, where a modification of the material structure in the sense of the desired deburring, or edge rounding, occurs as a result of the cumulative energy input. In the case of a small material thickness, for instance less than 0.2 mm, irradiation on one side may be sufficient in order to blunt both the shaped part edge facing toward the laser beam and the edge facing away, in one working step.

The laser beam 36 is moved over the holding part 18, which is for example only 1 mm wide, with a path speed of for example 20 mm/s, so that the individual irradiation intervals have only a short duration of for example 50 ms. There may be a waiting time between the irradiation intervals, in particular owing to successive beam guiding over an arrangement of a plurality of components. The energy input of the laser beam 36 in the individual irradiation intervals should be set below the threshold for material ablation, so that no melted drops are formed, or indeed no structural parts are destroyed. In this case, the number of irradiation intervals is expediently predetermined as a function of a desired edge dimension. For example, shaped part edges 28 having an edge radius of about 50 μm may be rounded in this way.

As shown in FIG. 4, in the mask etching method step, a multiplicity of microsamplers 10 may be produced in a desired arrangement and provided for magazining, for example in a circular disk magazine. In this case, the microsamplers 10 are formed in a star-shaped arrangement with tips 14 pointing radially outward and holding parts 18, made of a metal plate 42, lying on an inner circle.

Figure 5:
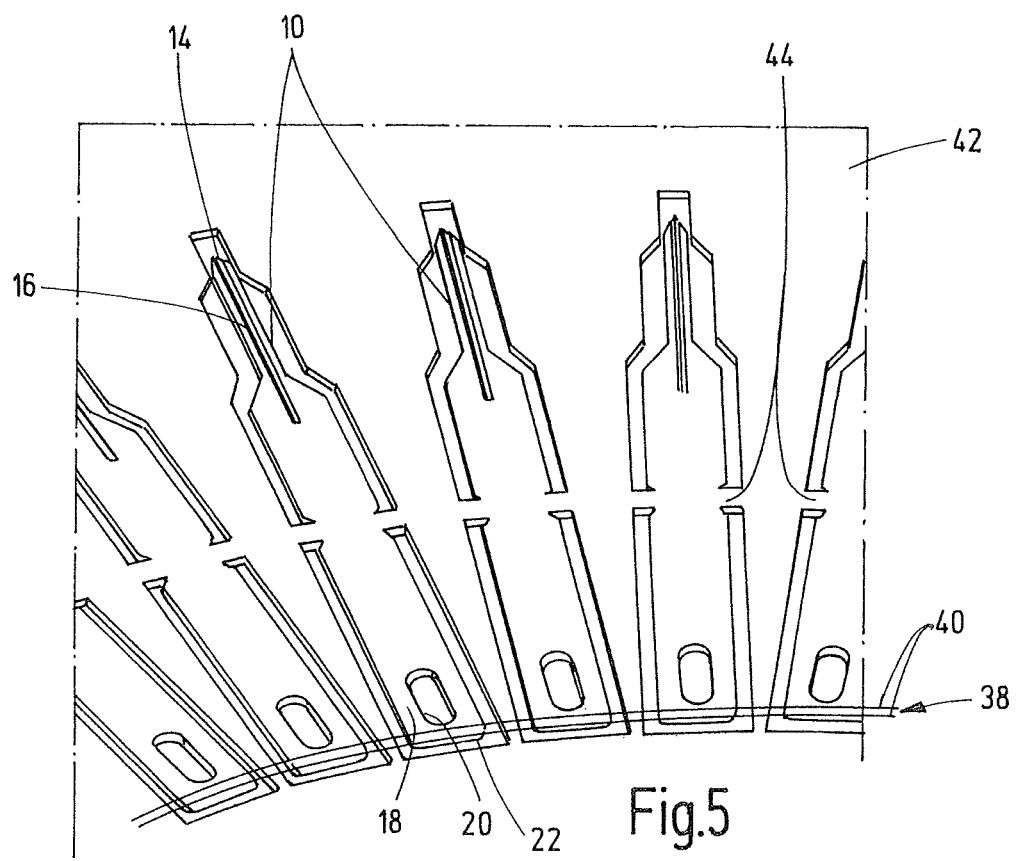
FIG. 5 shows a multitrack laser irradiation path for proximal edge rounding, in a detail of FIG. 4.

As can be seen from the detail enlargement according to FIG. 5, material separation along the shaped part edges may be carried out by a corresponding mask layout, the individual microsamplers 10 still being kept in a connected configuration for the subsequent laser irradiation in the etching grid by means of breakable material bridges 44. Subsequently, the laser beam 36 is guided in concentric circles 40 with decreasing diameter over the circularly coaxially arranged holding parts 18 toward the shaped part edges 22, in order to achieve the desired edge rounding.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention is claimed is:

1. A method for producing analytical aids for obtaining bodily fluid, comprising:
    forming the aids as a shaped part from a flat metallic material by material separation on shaped part edges; and
    finishing at least one sharp shaped part edge by laser irradiation, wherein said finishing includes
        guiding a laser beam repeatedly over the shaped part along an irradiation path in irradiation intervals, and
        rounding the shaped part edge by the cumulative energy input of the laser beam.

2. The method of claim 1 wherein said guiding includes guiding the laser beam into a region near the edge starting from a material region of the shaped part distant from the edge.

3. The method of claim 1 wherein said guiding includes guiding the laser beam on tracks laterally overlapping one another.

4. The method of claim 1 wherein said guiding includes guiding the laser beam in intervals with decreasing lateral offset from the shaped part edge.

5. The method of claim 1 wherein said forming includes arranging in a circular pattern the shaped part edges to be processed, of a multiplicity of shaped parts, and wherein said guiding includes guiding the laser beam on a spiral path or in concentric circles over the shaped parts to the shaped part edges to be deburred.

6. The method of claim 1 wherein said forming includes arranging in a linear pattern the shaped part edges to be deburred, of a multiplicity of shaped parts, and
    wherein said guiding includes scanning the shaped parts lying next to one another in lines with the laser beam.

7. The method of claim 1 wherein said forming includes forming a multiplicity of shaped parts in an integrated etching process from a flat material piece in a star-shaped or linear arrangement.

8. The method of claim 1 wherein said forming includes mask etching the aids as a shaped part.

9. The method of claim 1 wherein said forming includes forming the shaped parts with a sharp tip for insertion into the skin.

10. The method of claim 9 wherein said forming includes forming the shaped parts with a collecting channel for bodily fluid.

11. The method of claim 1 wherein said rounding includes rounding a shaped part edge in a coupling portion of the shaped parts formed for drive coupling.

12. The method of claim 1 wherein said finishing includes setting the energy input of the laser beam in the individual irradiation intervals below the threshold for material ablation.

13. The method of claim 1 wherein during said finishing the number of irradiation intervals is predetermined in accordance with a desired edge dimension of a shaped part edge.

14. The method of claim 1 wherein said rounding includes rounding the shaped part edge with an edge radius of more than 30 μm.

15. The method of claim 14 wherein said rounding includes rounding the shaped part edge with an edge radius of about 50 μm.

16. An analytical aid for obtaining bodily fluid, comprising a shaped part formed from a flat metallic material by mask etching wherein at least one shaped part edge is formed by being rounded by laser irradiation according to the method of claim 1.

17. The method of claim 7, wherein the multiplicity of shaped parts are connected by material bridges.

18. The method of claim 8, wherein said mask etching includes etching under a shaped part mask to form a burred sharp shaped part edge.

19. A method for producing analytical aids for obtaining bodily fluid, comprising:
    forming the aids by mask etching a metallic material, wherein each aid includes a sharp tip and a coupling portion configured to couple the aid to a drive, wherein the mask etching undercuts at the coupling portion to create a sharp edge at the coupling portion; and
    rounding the sharp edge at the coupling portion by guiding a laser beam on a multitrack irradiation path that extends in a lateral direction relative to the coupling portion, wherein the multitrack irradiation path during said rounding includes successive tracks of the laser beam that start distally of the sharp edge and progress towards the sharp edge.

20. The method of claim 19, wherein said rounding includes powering the laser beam at an energy level below a threshold where ablating of the metallic material occurs.

21. The method of claim 19, wherein:
    said forming includes forming the aids with the coupling portions aligned in a linear arrangement; and
    said rounding includes guiding the laser beam in a linear direction across the coupling portions of the aids.

22. The method of claim 21, wherein:
    said forming includes forming the aids in a circular pattern; and
    said rounding includes guiding the laser beam in a spiral pattern across the coupling portions of the aids.

* * * * *